US 9,052,401 B2

(12) United States Patent
Nakatsugawa et al.

(10) Patent No.: US 9,052,401 B2
(45) Date of Patent: Jun. 9, 2015

(54) RADIATION IMAGE DETECTION DEVICE AND RADIATION IMAGING SYSTEM

(71) Applicant: FUJIFILM Corporation, Tokyo (JP)

(72) Inventors: Haruyasu Nakatsugawa, Ashigarakami-gun (JP); Go Shirozu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/335,260

(22) Filed: Jul. 18, 2014

(65) Prior Publication Data

US 2015/0010130 A1 Jan. 8, 2015

Related U.S. Application Data

(63) Continuation of application No. PCT/JP2013/056447, filed on Mar. 8, 2013.

(30) Foreign Application Priority Data

Mar. 12, 2012 (JP) ................................. 2012-054507
Mar. 7, 2013 (JP) ................................. 2013-045386

(51) Int. Cl.
*G01T 1/20* (2006.01)
*A61B 6/00* (2006.01)
*G21K 4/00* (2006.01)
*C09K 11/77* (2006.01)

(52) U.S. Cl.
CPC ............... *G01T 1/2012* (2013.01); *G21K 4/00* (2013.01); *C09K 11/7771* (2013.01); *G01T 1/2008* (2013.01); *A61B 6/4216* (2013.01); *G01T 1/2018* (2013.01)

(58) Field of Classification Search
CPC ... G01T 1/2012; G01T 1/2008; G01T 1/2018; G21K 4/00; C09K 11/7771; A61B 6/4216
See application file for complete search history.

(56) References Cited

U.S. PATENT DOCUMENTS

| 7,227,167 B2 * | 6/2007 | Leblans et al. ................. 250/584 |
| 2002/0036267 A1 * | 3/2002 | Ikeda et al. ................. 250/361 R |
| 2005/0067586 A1 * | 3/2005 | Yanagita et al. ........... 250/484.4 |
| 2006/0202125 A1 * | 9/2006 | Suhami ......................... 250/368 |

FOREIGN PATENT DOCUMENTS

| JP | 62-212600 A | 9/1987 |
| JP | 2007-41008 A | 2/2007 |
| JP | 2010-112733 A | 5/2010 |

OTHER PUBLICATIONS

International Preliminary Report on Patentability, mailed Sep. 25, 2014, issued in PCT/JP2013/056447.
International Search Report, mailed Apr. 2, 2014, issued in PCT/JP2013/056447.
Written Opinion of the International Searching Authority, mailed Apr. 2, 2013, issued in PCT/JP2013/056447.

* cited by examiner

*Primary Examiner* — Irakli Kiknadze
(74) *Attorney, Agent, or Firm* — Birch, Stewart, Kolasch & Birch, LLP

(57) ABSTRACT

A radiation imaging system comprises a radiation source and a radiation image detection device. The radiation image detection device has a solid state detector and a wavelength converting layer arranged in this order from a radiation-incident side. The wavelength converting layer detects radiation passed through the solid state detector and converts the radiation into visible light. The solid state detector detects the visible light and produces image data. The wavelength converting layer is a phosphor layer, being a single layer, in which at least first phosphor particles having a first average particle diameter and second phosphor particles having a second average particle diameter are dispersed in a binder. The second average particle diameter is smaller than the first average particle diameter. The weight of the first phosphor particles per unit thickness of the wavelength converting layer decreases with increasing distance from the solid state detector.

14 Claims, 11 Drawing Sheets

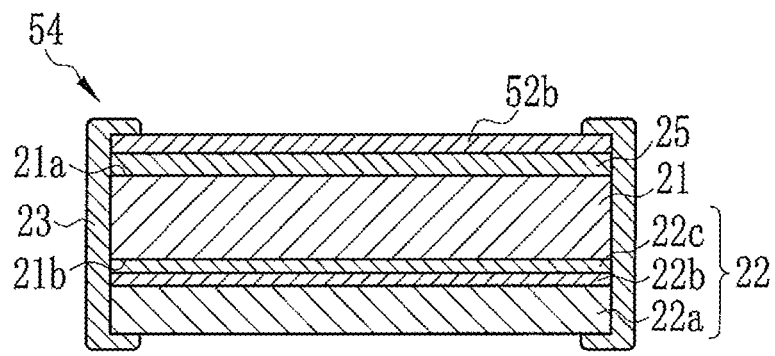
FIG. 8A
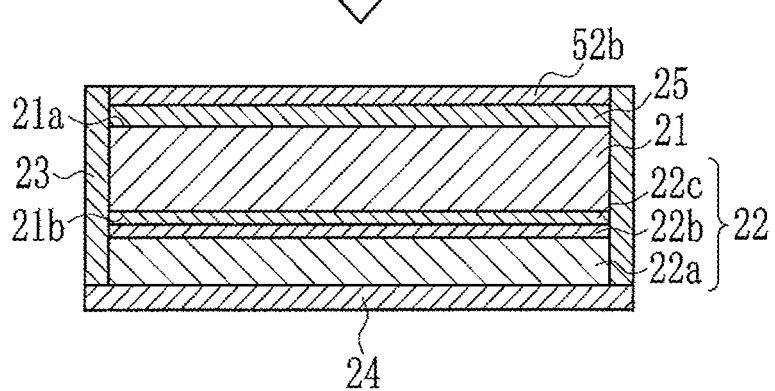
FIG. 8B
FIG. 9
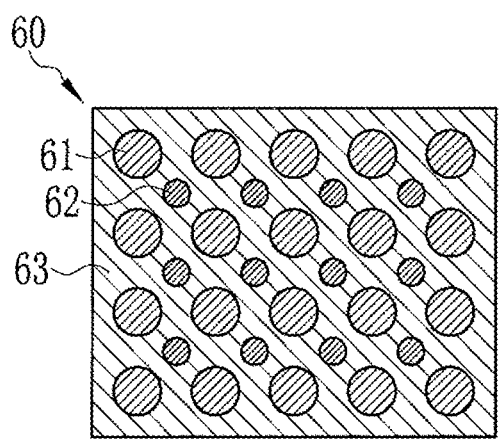

RADIATION IMAGE DETECTION DEVICE AND RADIATION IMAGING SYSTEM

CROSS-REFERENCE TO RELATED APPLICATIONS

This application is a Continuation of PCT International Application No. PCT/JP2013/056447 filed on Mar. 8, 2013, which claims priority under 35 U.S.C. §119(a) to Japanese Patent Application No. 2012-054507, filed Mar. 12, 2012 and Japanese Patent Application No. 2013-045386, filed Mar. 7, 2013. Each of the above applications is hereby expressly incorporated by reference, in its entirety, into the present application.

BACKGROUND OF THE INVENTION

1. Field of the invention

The present invention relates to an indirect conversion type radiation image detection device and a radiation imaging system having a radiation image detection device.

2. Description Related to the Prior Art

In a medical field or the like, a radiation imaging system is commonly used for observing the interior of a body cavity. The radiation imaging system comprises a radiation source and a radiation image detection device. The radiation source emits radiation such as X-rays to a subject. The radiation image detection device converts the radiation, which has passed through the subject, into a charge and then converts the charge into a voltage. Thereby the radiation image detection device produces image data, which represents a radiation image of the subject.

There are direct conversion type radiation image detection devices and indirect conversion type radiation image detection devices. The direct conversion type radiation image detection device directly converts the radiation into the charge. The indirect conversion type radiation image detection device converts the radiation into light (visible light) and then converts the light into the charge. The indirect conversion type radiation image detection device has a wavelength converting layer and a solid state detector. The wavelength converting layer converts the radiation into the light. The solid state detector converts the light, which has been generated by the wavelength converting layer, into the charge. The solid state detector has a plurality of photodiodes.

The wavelength converting layer contains phosphor for converting the radiation into the light. The phosphor is composed of particles (hereinafter referred to as phosphor particles) such as GOS($Gd_2O_2S$:Tb) or columnar crystals such as CsI:Tl. A wavelength converting layer of particle structure is commonly used because it is easier to manufacture and less expensive than that of columnar crystal structure. The wavelength converting layer of "particle structure" refers to a wavelength converting layer in which phosphor particles are dispersed in a binder such as resin.

The indirect conversion type radiation image detection device has the wavelength converting layer and the solid state detector stacked together, one on top of the other. There are two types of the indirect conversion type radiation image detection devices, depending on which one of the wavelength converting layer and the solid state detector is disposed close to the radiation source. The radiation image detection device with the wavelength converting layer close to the radiation source is referred to as PSS (Penetration Side Sampling) type. The radiation image detection device with the solid state detector close to the radiation source is referred to as ISS (Irradiation Side Sampling) type (See Japanese Patent Laid-Open Publication No. 2010-112733).

The wavelength converting layer emits the light in response to the radiation incident thereon. The light is mainly generated in a surface layer on which the radiation is incident. Hence, in the PSS type, the light is mainly generated in the surface layer on the opposite side of the solid state detector. The generated light propagates through the wavelength converting layer to the solid state detector. During the propagation, part of the light is absorbed by the wavelength converting layer or scattered. As a result, sensitivity (conversion efficiency for converting radiation into light) and sharpness of an image detected by the solid state detector are reduced.

In the ISS type, the radiation, which has passed through the solid state detector, is incident on the wavelength converting layer. Hence, the light is generated on a solid state detector side of the wavelength converting layer. The ISS type has advantages that the light propagation distance is short and thereby the reduction of the sensitivity and sharpness is suppressed.

To improve the sensitivity of the wavelength converting layer of the ISS type, the thickness of the wavelength converting layer is increased, for example. However, this increases a distance between the phosphor particles in the wavelength converting layer and the solid state detector. The phosphor particles generate the light at positions away from the solid state detector. The light from the phosphor particles spreads out significantly as the light propagates to the solid state detector, resulting in reduction of the image sharpness. The sensitivity of the wavelength converting layer is improved by increasing the size of the phosphor particles and thereby increasing the light emission amount of the phosphor particles. However, this further spreads out the light, which is emitted from the phosphor particles and propagates to the solid state detector. As a result, the sharpness is further reduced.

The Japanese Patent Laid-Open Publication No. 2010-112733 suggests a wavelength converting layer composed of a first phosphor layer, in which phosphor particles with a small average particle diameter are dispersed in a binder, and a second phosphor layer, in which phosphor particles with a large average particle diameter are dispersed in a binder. The first and second phosphor layers are layered or stacked together. The second phosphor layer is disposed on the solid state detector side. The second phosphor layer has the large-sized phosphor particles and high light emission amount, and is located close to the solid state detector. Hence, the spreading or scattering of the light is small and the reduction of the sharpness is prevented. In the first phosphor layer, the phosphor particles are away from the solid state detector, but the size of the phosphor particles is small. Hence, the spreading or scattering of the light is small and the reduction of the sharpness is prevented. As a result, the radiation image detection device is capable of improving the sensitivity without the reduction in sharpness.

However, in the radiation image detection device according to the Japanese Patent Laid-Open Publication No. 2010-112733, the wavelength converting layer has a two-layer structure, which is composed of the first and second phosphor layers, to improve the sensitivity and the sharpness. The two-layer structure increases manufacturing cost. For this reason, improvements of the sensitivity and the sharpness with the use of a single wavelength converting layer is desirable.

SUMMARY OF THE INVENTION

An object of the present invention is to provide an indirect conversion type radiation image detection device capable of improving sensitivity and sharpness while preventing increase in manufacturing cost and a radiation imaging system having a radiation image detection device.

In order to achieve the above and other objects, the radiation image detection device of the present invention comprises a wavelength converting layer for converting radiation into light and a solid state detector for detecting the light and thereby generating image data. The solid state detector and the wavelength converting layer are disposed in this order from a radiation-incident side on which the radiation from a radiation source is incident at the time of imaging. The wavelength converting layer is a single phosphor layer in which at least first phosphor particles and second phosphor particles are dispersed in a binder. The first phosphor particles have a first average particle diameter. The second phosphor particles have a second average particle diameter smaller than the first average particle diameter. The weight of the first phosphor particles per unit thickness of the wavelength converting layer decreases with increasing distance from the solid state detector.

It is preferable that the weight of the second phosphor particles per unit thickness of the wavelength converting layer is smaller on a solid state detector side than on an opposite side of the solid state detector.

It is preferable that the weight of the second phosphor particles per unit thickness of the wavelength converting layer increases with increasing distance from the solid state detector.

It is preferable that a phosphor coating liquid, in which the first and second phosphor particles are dispersed in a solution of the binder, is applied to a temporary support and dried and then peeled off from the temporary support and thereby the wavelength converting layer is formed. A surface of the wavelength converting layer on a temporary support side is placed on the solid state detector side.

It is preferable that a light reflective layer is provided over the wavelength converting layer and opposite the solid state detector. It is preferable that the wavelength converting layer has a protrusion on a surface on a light reflective layer side.

It is preferable that the solid state detector is bonded to the wavelength converting layer through a bonding agent layer or the solid state detector is directly in contact with and abut against the wavelength converting layer. It is preferable that a support is provided over the light reflective layer and opposite the wavelength converting layer. It is preferable that the wavelength converting layer and the support are bonded through the light reflective layer by heating and compression.

It is preferable that the weight ratio of the first phosphor particles to the second phosphor particles is 20% to 40%. It is preferable that the first average particle diameter is greater than or equal to 5 μm and less than or equal to 12 μm. It is preferable that the second average particle diameter is greater than or equal to 1 μm and less than 5 μm. It is preferable that a space-filling ratio of the first and second phosphor particles in the wavelength converting layer is greater than or equal to 68%.

It is preferable that the phosphor particles are formed of $A_2O_2S: X$, where A is one of Y, La, Gd, and Lu, and X is one of Eu, Tb, and Pr.

It is preferable that the radiation image detection device further comprises a side covering member for covering outer edges of the wavelength converting layer.

The radiation imaging system of the present invention comprises a radiation source and a radiation image detection device. The radiation source applies radiation to a subject. The radiation image detection device detects a radiation image based on the radiation passed through the subject. The radiation image detection device comprises a wavelength converting layer for converting the radiation into light and a solid state detector for detecting the light and thereby generating image data of the radiation image. The wavelength converting layer is a single phosphor layer in which at least first phosphor particles and second phosphor particles are dispersed in a binder. The first phosphor particles have a first average particle diameter. The second phosphor particles have a second average particle diameter smaller than the first average particle diameter. The solid state detector and the wavelength converting layer are disposed such that the radiation passed through the solid state detector is incident on the wavelength converting layer. The weight of the first phosphor particles per unit thickness of the wavelength converting layer decreases with increasing distance from the solid state detector.

According to the present invention, the wavelength converting layer is a single phosphor layer in which at least the first phosphor particles and the second phosphor particles are dispersed in the binder. The first phosphor particles have the first average particle diameter. The second phosphor particles have the second average particle diameter, which is smaller than the first average particle diameter. The weight of the first phosphor particles per unit thickness of the wavelength converting layer decreases with increasing distance from the solid state detector. As a result, the sensitivity and the sharpness are improved.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIGS. 8A and 8B illustrate further subsequent steps for producing the radiation image detection device;

FIG. 9 is a lateral cross-sectional view cutting a wavelength converting layer of a second embodiment in a direction orthogonal to the radiation;

DESCRIPTION OF THE PREFERRED EMBODIMENTS

First Embodiment

Figure 1:
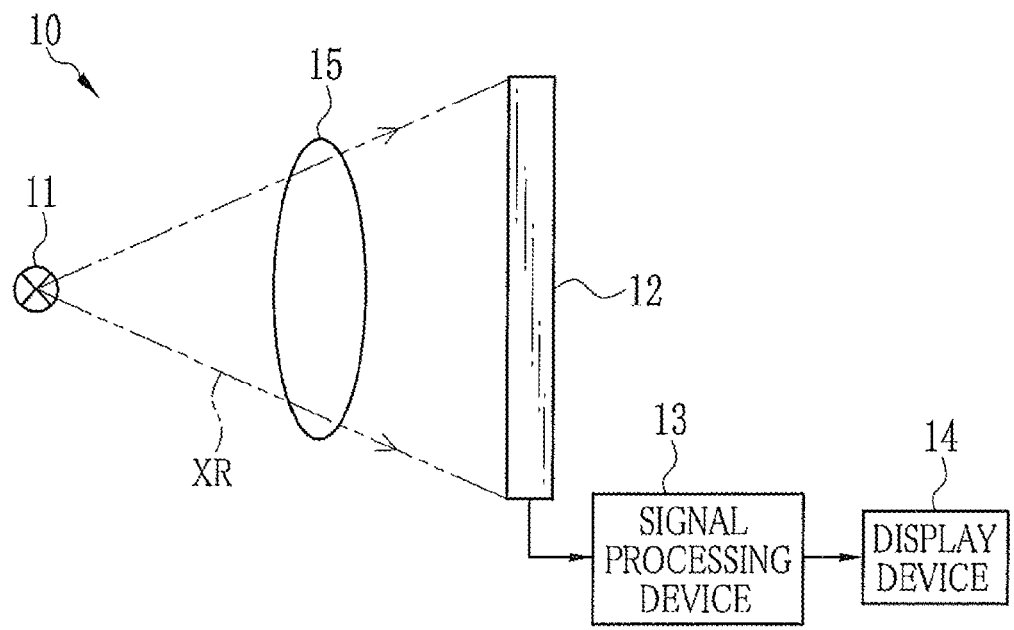
FIG. 1 is an explanatory view of a radiation imaging system.

In FIG. 1, a radiation imaging system 10 comprises a radiation source 11, a radiation image detection device 12, a signal processing device 13, and a display device 14. The radiation source 11 applies radiation (for example X-rays) XR to a subject 15. The radiation image detection device 12 detects the radiation XR, which has passed through the subject 15, and thereby detects a radiation image of the subject 15 carried by the radiation XR. Thus, the radiation image detection device 12 produces and outputs image data of the radiation image. The signal processing device 13 performs predetermined signal processing on the image data outputted from the radiation image detection device 12. The display device 14 displays the radiation image based on the image data which has been subjected to the signal processing in the signal processing device 13.

Figure 2:
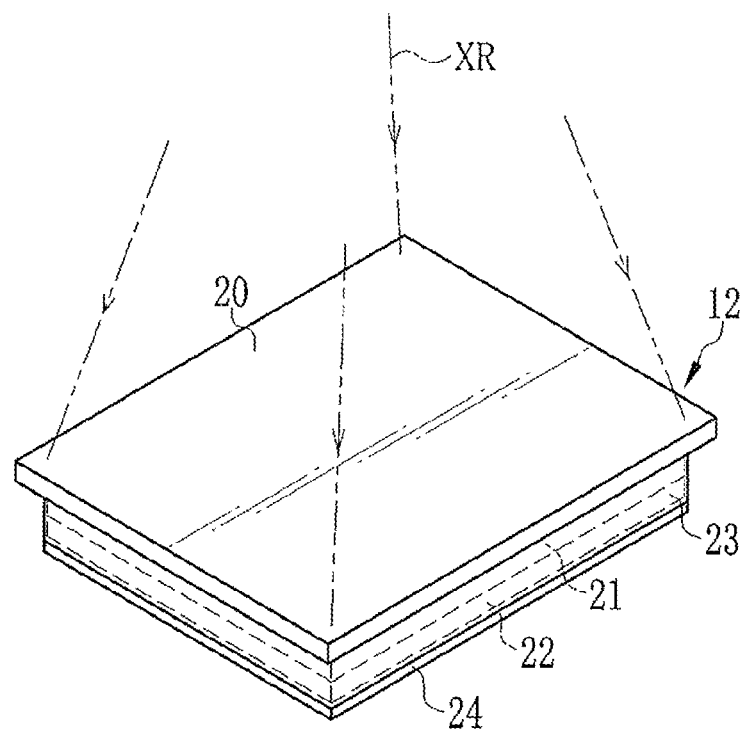
FIG. 2 is a perspective view of a radiation image detection device.

In FIG. 2, the radiation image detection device 12 is composed of a solid state detector 20, a wavelength converting layer 21, a support 22, a side covering member 23, and a protective layer 24. The solid state detector 20, the wavelength converting layer 21, the support 22, and the protective layer 24 are layered or stacked in this order from the radiation source 11 side. The radiation XR from the radiation source 11 passes through the subject 15 and then the solid state detector 20, and then enters the wavelength converting layer 21. A radiation shield plate (not shown) such as a lead plate is provided on the opposite side of the radiation-incident side of the protective layer 24.

The wavelength converting layer 21 is a phosphor layer (scintillator), being a single layer, that converts the radiation XR, which is incident thereon at the time of imaging, into light (visible light). The solid state detector 20 detects the light converted by the wavelength converting layer 21 and thereby generates image data which represents a radiation image. The side covering member 23 covers the outer edges (sides) of the wavelength converting layer 21 and the support 22. The protective layer 24 covers the surface, of the support 22, opposite to the wavelength converting layer 21.

The radiation image detection device 12 is used in the form of an electronic cassette, which is attached to an imaging table in a detachable manner. In the electronic cassette, the radiation image detection device 12 is accommodated in a housing (not shown). An image memory and a battery (both not shown) are also accommodated in the housing. An alignment mark (not shown) is provided on a surface, of the housing, on the radiation-incident side. The alignment mark is used for aligning the housing with the radiation source 11 and the subject 15.

Figure 3:
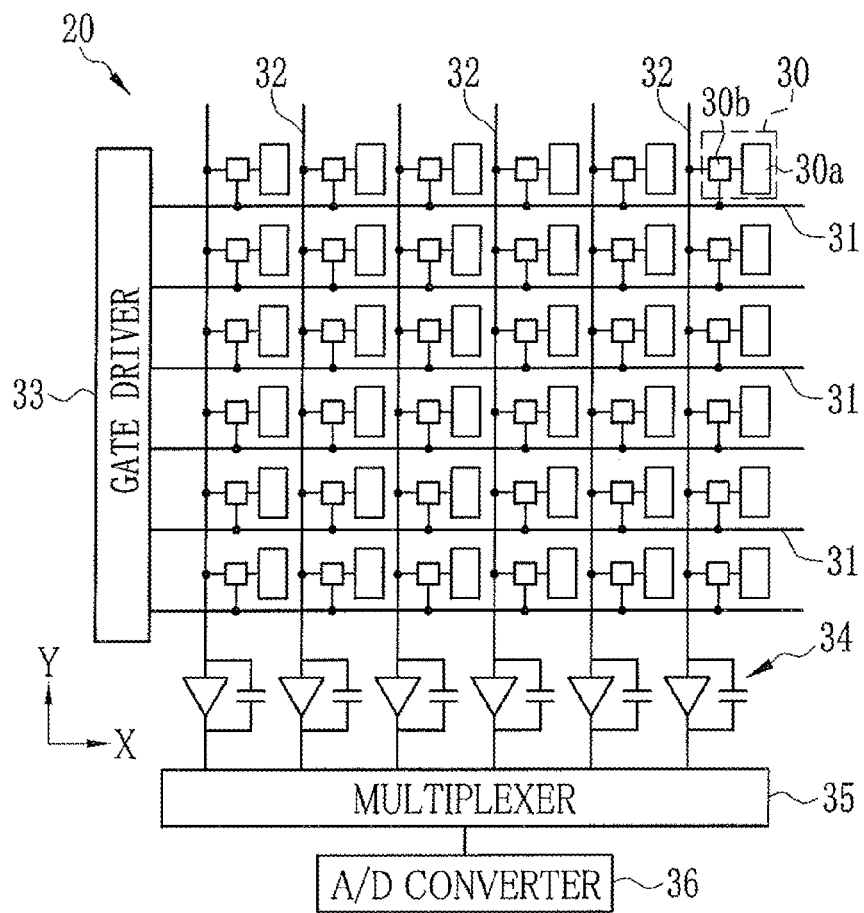
FIG. 3 is an explanatory view of a solid state detector.

In FIG. 3, the solid state detector 20 comprises a plurality of pixels 30, a plurality of scanning lines 31, a plurality of data lines 32, a gate driver 33, integration amplifiers 34, a multiplexer 35, and an A/D converter 36. The pixel 30 is composed of a photodiode 30a and a TFT switch 30b. The pixels 30 are arranged in two-dimensions in X and Y directions. The scanning line 31 is provided for each row of the pixels 30 arranged in the X direction. A scanning signal for driving the TFT switch 30b is supplied to the scanning line 31. The data line 32 is provided for each column of the pixels 30 arranged in the Y direction. A signal charge, which is stored in the photodiode 30a and read out through the TFT switch 30b, is transmitted through the data line 32.

The photodiode 30a generates a signal charge in response to light, which is generated by the wavelength converting layer 21, and stores the signal charge. The TFT switch 30b is provided at each intersection of the scanning line 31 and the data line 32. The TFT switch 30b is connected to the photodiode 30a.

The gate driver 33 is connected to an end of each scanning line 31. The gate driver 33 sequentially supplies the scanning signals to the respective scanning lines 31. The integration amplifier 34 is connected to an end of each data line 32. The integration amplifier 34 integrates the signal charge transmitted through each data line 32 and outputs a voltage which corresponds to an integrated charge amount. The multiplexer 35 is provided on the output side of the integration amplifiers 34. The multiplexer 35 selectively inputs the voltage, which is outputted from the integration amplifier 34, to the A/D converter 36. The A/D converter 36 converts the voltage, which is inputted from the integration amplifier 34 through the multiplexer 35, into a digital signal. A voltage amplifier and the like are provided between the integration amplifier 34 and the A/D converter 36. The digital signals corresponding to all the pixels, which are outputted from the A/D converter 36, constitute the image data.

Figure 4:
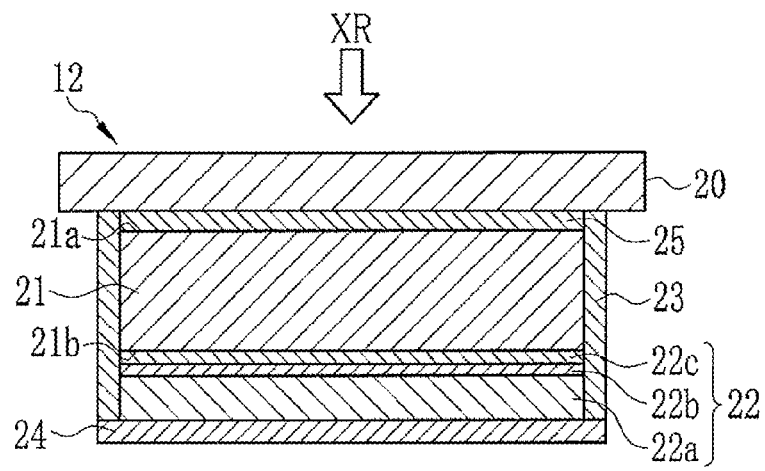
FIG. 4 is a vertical cross-sectional view cutting the radiation image detection device in a direction of radiation.

In FIG. 4, a first surface 21a of the wavelength converting layer 21 is bonded to the solid state detector 20 through a bonding agent layer 25. A second surface 21b of the wavelength converting layer 21 is bonded to the support 22. The bonding agent layer 25 is formed of an acrylic type material. The support 22 is composed of a resin film 22a, a conductive layer 22b, and a light reflective layer 22c, which are layered or stacked in this order from the bottom. The second surface 21b of the wavelength converting layer 21 is bonded to the light reflective layer 22c. The bottom surface of the support 22 is covered with the protective layer 24.

The side covering member 23 is formed of resin or the like. It is preferable that the thickness of the side covering member 23 is greater than or equal to 5 μm and less than or equal to 500 μm. The side covering member 23 is, for example, a hard coating composed of silicone type polymer and polyisocyanate.

In the silicone type polymer, one component (polymer, prepolymer, or monomer) mainly containing polysiloxane unit and the other component (polymer, prepolymer, or monomer) are bonded alternately or in a block or pendant through condensation reaction or polyaddition reaction. Examples of such polymer include polyurethane having the polysiloxane unit, polyurea having the polysiloxane unit, polyester having the polysiloxane unit, and acrylic resin having the polysiloxane unit.

The polyisocyanate is a compound, for example, various types of polyisocyanate monomer, an adduct of polyol such as TMP (trimethylol propane) and isocyanate such as TDI (tolylene diisocyanate) or polyisocyanate, polymer such as polymer of dimer or trimer of TDI and polymer of HMDI (hexamethylene diisocianate), an isocyanate prepolymer which is formed by a reaction between polyisocyanate and a polyfunctional hydroxyl compound or amine compound or a reaction between polyisocyanate and hydroxy polyether or polyester, or the like. Generally, a mixture ratio (polymer: polyisocyanate) between the silicone type polymer and polyisocyanate is 99:1-10:90 (weight ratio). The mixture ratio is preferably 95:5-20:80, and more preferably 90:10-70:30.

Polyethylene terephthalate (PET), cellulose acetate, polyester, polyamide, polyimide, triacetate, polycarbonate, or the like is used as the material of the resin film 22a of the support 22. The thickness of the resin film 22a is preferably greater than or equal to 20 μm and less than or equal to 2 mm, and more preferably greater than or equal to 70 μm and less than or equal to 0.5 mm.

The conductive layer 22b is a dispersion of a conductive agent such as $SnO_2$ in resin such as polyester. The light reflective layer 22c is a dispersion of a light-reflective material such as alumina particles in resin such as acrylic resin. The Super Barrier Film (trade name: SBF) manufactured by FUJIFILM Corporation is used as the protective layer 24.

The side covering member 23 may be conductive. For example, conductive particles such as $SnO_2$:Sb or ZnO, carbon cluster such as carbon black, fullerenes, carbon nanotubes or the like may be mixed to polymer. In this case, it is preferable that the sheet resistance of the side covering member 23 is less than or equal to $10^8 \Omega$.

Figure 5:
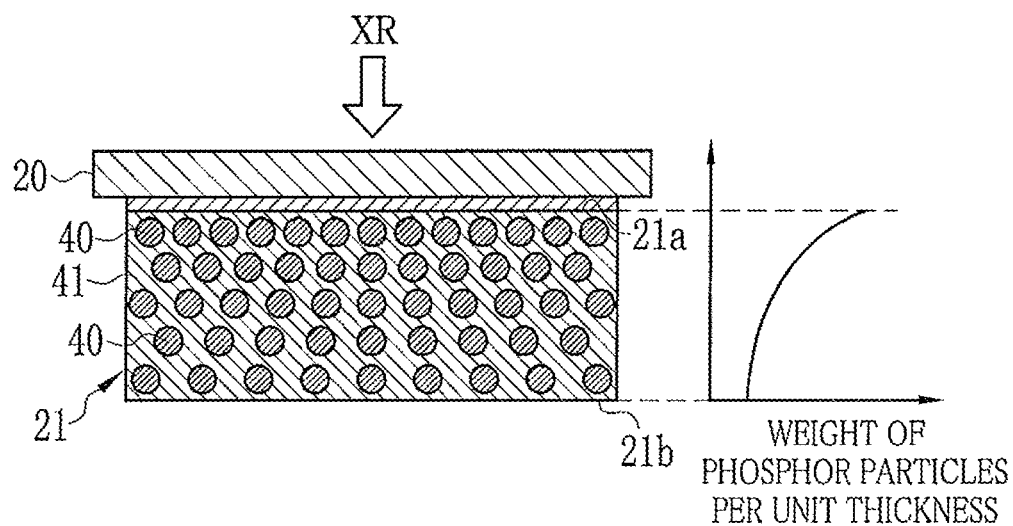
FIG. 5 is an explanatory view illustrating a wavelength converting layer.

In FIG. 5, the wavelength converting layer 21 is formed by dispersing phosphor particles 40 such as GOS($Gd_2O_2S$:Tb) in a binder 41 such as resin. The phosphor particles 40 are shown in spherical shape, but they actually have distorted polygonal shapes. The average particle diameter of the phosphor particles 40 is in the order of 5 μm. Here, the average particle diameter refers to an average of the particle diameters measured by Fisher Sub-Sieve Sizer method, for example.

The phosphor particles 40 are particles represented by $A_2O_2S$: X, where A is one of Y, La, Gd, and Lu, and X is one of Eu, Tb, and Pr. The phosphor particles 40 may be $A_2O_2S$:X containing cerium (Ce) or samarium (Sm) as a co-activator. The phosphor particles 40 may be mixed-crystal type phosphor.

The weight of the phosphor particles 40 per unit thickness of the wavelength converting layer 21 gradually decreases from a first surface 21a side toward a second surface 21b side, which is opposite to the radiation (XR) incident side. On the contrary, the weight of the binder 41 per unit thickness of the wavelength converting layer 21 gradually increases from the first surface 21a side toward the second surface 21b side. Hence, the space-filling ratio of the phosphor particles 40 is high on the solid state detector 20 side. The space-filling ratio of the phosphor particles 40 is low at a position apart from the solid state detector 20. Thereby, a light emission amount of the wavelength converting layer 21 is high on the solid state detector 20 side and spreading or scattering of the light from the phosphor particles 40 to the solid state detector 20 is suppressed. As a result, the sensitivity and sharpness of an image captured with the solid state detector 20 are improved.

It is preferable that the space-filling ratio of the phosphor particles 40 in the wavelength converting layer 21 is greater than or equal to 63%. Generally, the space-filling ratio of the phosphor (phosphor particles) is calculated as follows. First, a part of the wavelength converting layer 21 is cut out and then the volume thereof is measured. Next, the weight of the phosphor, which is extracted from the cut out wavelength converting layer 21 with the use of a solvent or the like, is measured. The volume of the phosphor is calculated from the density of the phosphor. The space-filling ratio is represented by the ratio between the volume of the phosphor and the volume of the cut out wavelength converting layer 21. Note that, in the case where the composition of the phosphor is unknown, composition analysis may be performed. The density may be calculated from constituent elements and crystal structure.

Figure 6A:
FIGS. 6A and 6B illustrate initial steps for producing the radiation image detection device.

Next, a method for producing the radiation image detection device 12 is described. First, as shown in FIG. 6A, a release agent, for example, a silicone-type release agent is applied to a surface of a temporary support 50 formed of resin such as PET, and thereby a release agent layer 51 is formed.

Figure 6B:
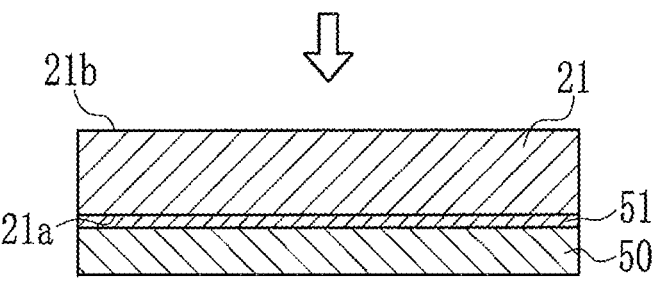

As shown in FIG. 6B, a phosphor coating liquid, in which the phosphor particles 40 are dispersed in a solution (binder solution) of the binder 41, is applied to the release agent layer 51 with the use of a doctor blade. The phosphor coating liquid includes a volatile solvent (MEK or the like). The phosphor coating liquid on the release agent layer 51 is dried, and thereby the wavelength converting layer 21 is formed as a phosphor sheet. When the phosphor coating liquid is applied, sedimentation of the phosphor particles 40 occurs due to their high specific gravity in the solution of the binder 41. Due to the sedimentation, the phosphor particles 40 move or sink toward the temporary support 50 side (the first surface 21a side). The drying further promotes the sinking of the phosphor particles 40. As a result, the weight of the binder 41 per unit thickness of the wavelength converting layer 21 gradually decreases from the opposite side of the temporary support 50 (the second surface 21b side) toward the temporary support side 50 (the first surface 21a side).

Figure 7A:
FIGS. 7A-7E illustrate subsequent steps for producing the radiation image detection device.
Figure 7B:
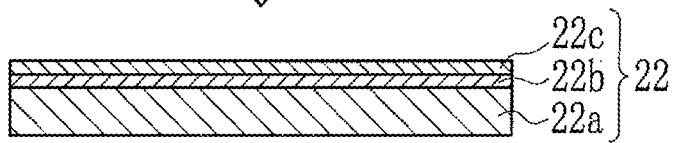

As shown in FIG. 7A, a conductive coating liquid is applied to a surface of the resin film 22a, which is formed of resin such as PET, and then dried and hardened. Thereby the conductive layer 22b is formed. As shown in FIG. 7B, a coating layer in which a light reflection material is dispersed is applied to the conductive layer 22b with the use of a doctor blade, and dried. Thereby the light reflective layer 22c is formed. Thus, the support 22 is completed.

Figure 7C:
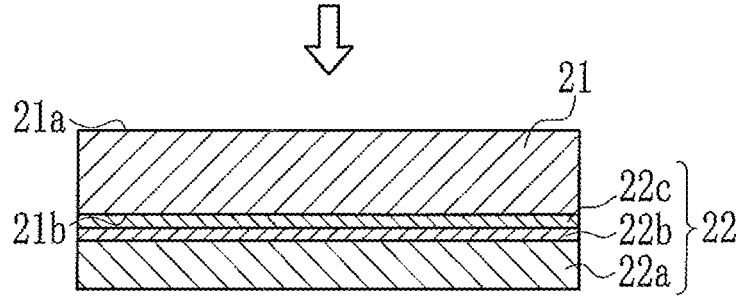

Then, the wavelength converting layer 21, which is produced through the step(s) shown in FIG. 6B, is peeled off from the temporary support 50. As shown in FIG. 7C, the wavelength converting layer 21 is layered or stacked over the support 22 such that the second surface 21b comes in contact with the light reflective layer 22c. Then a calendaring machine is used to heat and compress the wavelength converting layer 21 and the support 22 in the stacked state. Thereby the second surface 21b of the wavelength converting layer 21 is fused to the light reflective layer 22c. An amount of the binder 41 in the second surface 21b of the wavelength converting layer 21 is greater than an amount of the binder 41 in the first surface 21a of the wavelength converting layer 21. Hence, an amount of the binder 41 fused is greater in the second surface 21b than in the first surface 21a during the heating and compression. As a result, the second surface 21b has excellent adhesion to the light reflective layer 22c.

Figure 7D:
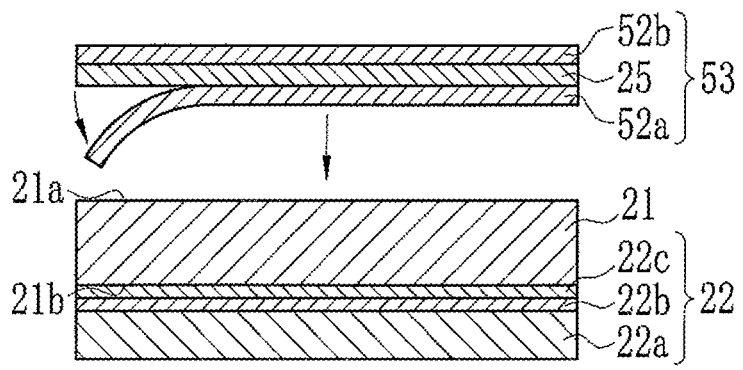
Figure 7E:
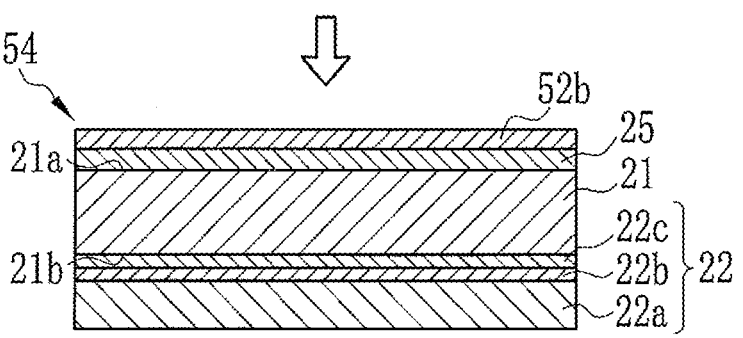

As shown in FIG. 7D, an adhesive sheet 53, which is composed of a first release film 52a, the bonding agent layer 25, and a second release film 52b layered or stacked in this order, is prepared. Then the first release film 52a is peeled off. As shown in FIG. 7E, the bonding agent layer 25 is bonded to the wavelength converting layer 21. The bonding agent layer 25 is formed of an acrylic bonding agent. The first and second release films 52a and 52b are formed of PET liners.

A radiation converting sheet 54, which is produced through the above-described steps, is cut to the specified size. As shown in FIG. 8A, after the cutting, the side covering member 23 is applied to the sides (the outer edges) of the radiation converting sheet 54 with the use of a dispenser. The side covering member 23 covers the outer edges (sides) from the second release film 52b to the resin film 22a. As shown in FIG. 8B, the protective layer 24 is formed on the bottom surface of the resin film 22a.

Then the second release film 52b is peeled off. The first surface 21a of the wavelength converting layer 21 is bonded to the surface of the solid state detector 20, which is produced through a well-known semiconductor process, through the bonding agent layer 25. To be more specific, first, dust is removed from the surface of the bonding agent layer 25 with the use of an ionizer when the second release film 52b is peeled off. Then the radiation converting sheet 54 and the solid state detector 20 are bonded together through the bonding agent layer 25 with the use of a bonding machine. Thereafter, a roller presses the back surface of the solid state detector 20. Thereby the solid state detector 20 is bonded to the wavelength converting layer 21. Thus, the radiation image detection device 12 is completed.

Cutting the radiation converting sheet 54 or forming the side covering member 23 may cause dirt or dust. The dirt or dust is deposited on the second release film 52b, but removed together with the second release film 52b when the second release film 52b is peeled off. Even if the side covering member 23 is formed to partly extend above the outer edges of the second release film 52b, the excess part of the side covering member 23 is removed together with the second release film 52b when the second release film 52b is peeled off. Hence, the side covering member 23 is eliminated from between the wavelength converting layer 21 and an area of the solid state detector 20 in which the pixels 30 are arranged.

The first surface 21a of the wavelength converting layer 21 is bonded to the solid state detector 20 through the bonding agent layer 25. Although the first surface 21a contains a small amount of the binder 41, the adhesion of the wavelength converting layer 21 to the solid state detector 20 is ensured because they are bonded through the bonding agent layer 25.

Next, an operation of the radiation imaging system 10 is described. First, the radiation source 11 emits the radiation XR to the subject 15. The radiation XR passes through the subject 15 and thereby carries a radiation image of the subject 15. The radiation XR is incident on the surface, of the radiation image detection device 12, on the solid state detector 20 side. The radiation XR, which entered the radiation image detection device 12, passes through the solid state detector 20 and then incident on the first surface 21a of the wavelength converting layer 21. The wavelength converting layer 21 converts the incident radiation XR into light (visible light).

Here, the amount of the binder 41 on the first surface 21a side of the wavelength converting layer 21 is small. The space-filling ratio of the phosphor particles 40 on the first surface 21a side is large. Hence, the light emission amount of the phosphor particles 40 is high and spreading or scattering of the light from the phosphor particles 40 to the solid state detector 20 is small in the proximity of the solid state detector 20. Furthermore, propagation of the light in a lateral direction (a direction orthogonal to the direction of incidence of the radiation XR) through the binder 41 is suppressed on the first surface 21a side, due to the small amount of the binder 41.

The light converted by the wavelength converting layer 21 is incident on the solid state detector 20. The solid state detector 20 performs photoelectric conversion. Each pixel 30 stores a signal charge generated by the photoelectric conversion. The solid state detector 20 reads out the signal charge stored in each pixel 30. The solid state detector 20 converts the signal charges of one screen into image data and outputs the image data.

The image data outputted from the solid state detector 20 is inputted to the signal processing device 13. The image data is subjected to signal processing in the signal processing device 13 and then inputted to the display device 14. The display device 14 displays an image based on the inputted image data.

Hereinafter, examples for forming the radiation converting sheet 54 are described.

Example 1

1) Formation Of Wavelength Converting Layer

Twenty wt % of a mixture of polyvinyl butyral (PVB) resin, urethane resin, and a plasticizer is dissolved into 80 wt % of a mixed solvent of toluene, 2-butanol, and xylene, and stirred sufficiently. Thereby a binder solution is prepared.

The binder solution and $Gd_2O_2S$: Tb phosphor (solid component) with the average particle diameter of 5 μm are mixed at a mass % ratio of 15:85, and then dispersed with a ball mill (ball grinder). Thus the phosphor coating liquid is prepared.

The phosphor coating liquid (width: 430 mm) is applied to a surface of PET coated with a silicone-type releasing agent (that is, the temporary support, thickness: 190 μm) with the use of a doctor blade and dried, and then peeled off from the temporary support. Thereby a wavelength converting layer (thickness: 300 μm) is produced.

2) Formation of the Conductive Layer

MEK (methyl ethyl ketone) 5 g is added to the material with the composition below, and mixed and dispersed. Thereby a coating liquid is prepared. The coating liquid is applied to a surface of PET (support, thickness: 188 μm, haze 27%, LUMIRROR (registered trademark) S-10 manufactured by TORAY INDUSTRIES, INC.) with the use of a doctor blade, and dried and hardened. Thereby the conductive layer (film thickness: 5 μm) is formed.

Resin: MEK solution (solid content 30 wt %) of saturated polyester resin (VYLON 300 (registered trademark) manufactured by TOYOBO Co., Ltd.) 20 g Hardener: polyisocyanate (OLESTER NP38-705 (registered trademark) manufactured by Mitsui Toatsu Chemicals Inc., solid content 70%) 2 g Conductive agent: MEK dispersion (solid content 30 wt %) of needle-like (Sb-doped) $SnO_2$ particles 50 g 3) Formation of the Light Reflective Layer A material with the composition below is added to MEK 387 g, and mixed and dispersed. Thereby a coating liquid is prepared. The coating liquid is applied to a surface of the conductive layer with the use of a doctor blade, and dried. Thereby the light reflective layer (film thickness: approximately 100 μm) is formed.

Light reflective material: high purity alumina particles (average particle diameter: 0.4 μm) 444 g Binder: soft acrylic resin (CRISCOAT P-1018GS(registered trademark) manufactured by DIC Corporation, 20% toluene solution) 100 g 4) Bonding of the Wavelength Converting Layer and the Light Reflective Layer The wavelength converting layer prepared in the step 1) is stacked over the surface of the light reflective layer such that the upper surface (the surface opposite the temporary support) of the wavelength converting layer comes in contact with the light reflective layer, and then heated and compressed with the calendaring machine (total load 2300 kg, upper role 45° C., lower role 45° C., feeding speed 0.3 m/min) Thereby the wavelength converting layer is completely fused to the light reflective layer. The thickness of the layer after the heating and compression is 200 μm.

5) Formation of the Bonding Agent Layer and Release Film(s)

The adhesive sheet is composed of a PET liner (38 μm) (light release type), an acrylic type bonding agent layer (15 μm), and a PET liner (75 μm) (heavy release type), stacked in this order. The light release type release film (liner) is peeled off, and then the bonding agent layer is bonded to the phosphor layer.

6) Formation of the Side Covering Member

The radiation converting sheet produced through steps 1) to 5) is cut to the specified size, and then set to the dispenser for the side covering member. A robot is controlled to cover the sides (the outer edges) of the phosphor layer with the side covering member. A coating liquid which is prepared by dissolving the mixture with the composition below in methyl ethyl ketone 150 g is used for forming the side covering member.

Silicone type polymer: polyurethane having polydimethylsiloxane unit (Dainichi Seika Color and Chemicals Manufacturing Co., Ltd., DAIALLOMER SP3023 [15% methyl ethyl ketone solution]) 700 g Cross linking agent: polyisocyanate (Dainichi Seika Color and Chemicals Manufacturing Co., Ltd., CROSSNATE D-70 [50% solution])30 g Yellowing preventing agent: epoxy resin (Yuka-Shell Epoxy Co., Ltd., EPICOAT #1001 [solid]) 6 g Lubricant: alcohol modified silicone (Shin-Etsu Chemical Co., Ltd., X-2 2-2809 [paste containing 66% xylene]) 2 g The produced coating liquid is applied all over the edges (including 1 mm inside each edge) of the radiation converting sheet, which has subjected to corona discharge processing, and dried sufficiently at room temperature. Thus, edge coating with the film thickness of approximately 25 μm is formed.

Second Embodiment

In the first embodiment, the phosphor particles 40 of substantially the same size are dispersed in the binder 41 and thereby the wavelength converting layer 21 is formed. In a second embodiment, as shown in FIG. 9, first and second phosphor particles 61 and 62 which differ in size are dispersed in a binder 63 and thereby a wavelength converting layer 60 is formed. The configuration of the radiation image detection device of the second embodiment is the same as that of the radiation image detection device 12 of the first embodiment except that the wavelength converting layer 60 is used instead of the wavelength converting layer 21.

The average particle diameter D1 of the first phosphor particles 61 is greater than the average particle diameter D2 of the second phosphor particles 62. The average particle diameter D1 of the first phosphor particles 61 is preferably greater than or equal to 5 μm and less than or equal to 12 μm, and more preferably in the order of 6 μm. The average particle diameter D2 of the second phosphor particles 62 is preferably greater than or equal to 1 μm and less than 5 μm and more preferably in the order of 2 μm. In this embodiment, the second phosphor particles 62 enter the spaces between the first phosphor particles 61 with the large average particle diameter and become embedded in the spaces. Thus, the space-filling ratio of the phosphor is improved, resulting in improvement of the image quality.

The first phosphor particles 61 and the second phosphor particles 62 may be formed of the same material, for example, GOS. The material of the first phosphor particles 61 may differ from the material of the second phosphor particles 62, for example, the first phosphor particles 61 may be formed of GOS and the second phosphor particles 62 may be formed of LOS($Lu_2O_2S$:Tb).

Figure 10:
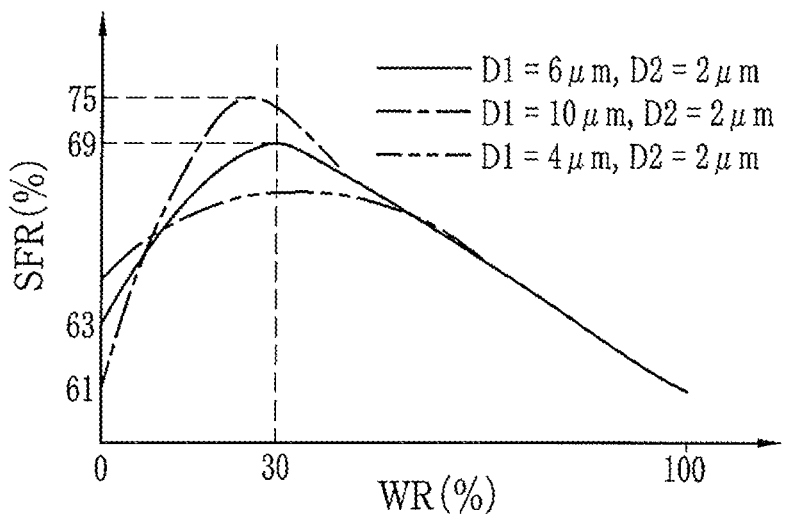
FIG. 10 is a graph illustrating a relationship between space-filling ratio of first and second phosphor particles and weight ratio.

In the wavelength converting layer 60, a space-filling ratio SFR of the first and second phosphor particles 61 and 62 is dependent on a weight ratio WR of the second phosphor particles 62 to the first phosphor particles 61. In FIG. 10, a solid line represents the space-filling ratio SFR where D1=6 μm and D2=2 μm and shows that the space-filling ratio SFR is at the maximum in a case where the weight ratio WR is approximately 30%. In this case, it is preferable that the weight ratio WR is in a range from 20% to 40%. In this range, the space-filling ratio SFR is greater than or equal to approximately 68%.

Alternate long and short dashed lines represent a space-filling ratio SFR of the case where D1=10 μm and D2=2 μm. A chain double-dashed line represents a space-filling ratio SFR of the case where D1=4 μm and D2=2 μm. Thus, the greater the average particle diameter D1 of the first phosphor particles 61, the easier the second phosphor particles 62 are embedded in the spaces between the first phosphor particles 61. As a result, the space-filling ratio SFR is improved.

Figure 11:
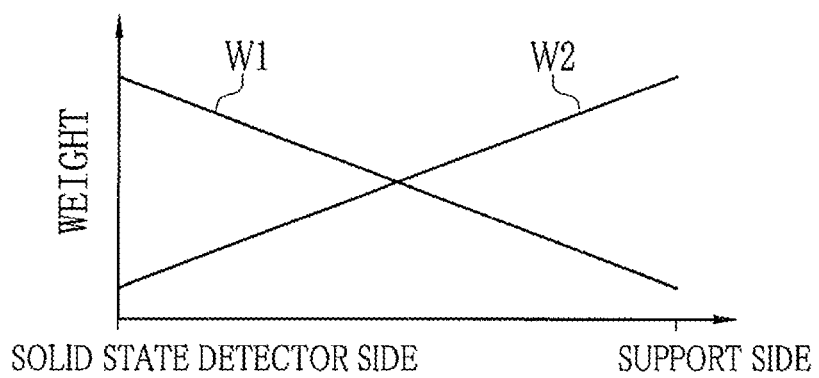
FIG. 11 is a graph illustrating changes in weight of the first and second phosphor particles in a thickness direction of the wavelength converting layer.

In FIG. 11, the weight W1 of the first phosphor particles 61 per unit thickness of the wavelength converting layer 60 gradually decreases from the solid state detector 20 side toward the support 22 side. Namely, the weight W1 decreases with increasing distance from the solid state detector 20. On the contrary, the weight W2 of the second phosphor particles 62 per unit thickness of the wavelength converting layer 60 gradually increases from the solid state detector 20 side toward the support 22 side. Namely, the weight W2 increases with increasing distance from the solid state detector 20. Thus, the first phosphor particles 61 with the large average particle diameter are mainly present on the solid state detector 20 side. The second phosphor particles 62 with the small average particle diameter are mainly present on the support 22 side. As a result, an image with high sensitivity and high sharpness is produced. Note that, in FIG. 11, distribution of weights is depicted schematically with straight lines, but actually, they are curved lines.

To produce the wavelength converting layer 60, a phosphor coating liquid, in which the first phosphor particles 61 and the second phosphor particles 62 are dispersed in the binder 63, is applied to the temporary support and dried. Thereby the first phosphor particles 61 with the large average particle diameter move or sink toward the temporary support side due to sedimentation. Since the first phosphor particles 61 mostly occupy the temporary support side of the phosphor coating liquid (the wavelength converting layer 60), part of the second phosphor particles 62 with the small average particle diameter enter the spaces between the first phosphor particles 61 and become embedded in the spaces. The remainder of the second phosphor particles 62 moves to the opposite side of the temporary support side. Thereby the above-described distribution of the weights is obtained. The weight of the binder 63 per unit thickness of the wavelength converting layer 60 gradually decreases from the opposite side of the temporary support side toward the temporary support side, in a manner similar to the first embodiment.

The amount of the first phosphor particles 61 moving to the temporary support side is adjusted by controlling drying conditions of the phosphor coating liquid. For example, in the case where the phosphor coating liquid is dried slowly in a long period of time, the amounts of the movements of the first phosphor particles 61 toward the temporary support side are increased. As a result, the space filling ratio of the first phosphor particles 61 is further increased on the temporary support side.

The temperature of the phosphor coating liquid is slightly increased (for example, the temperature is raised to 25° C. or 30° C. in the case where the normal temperature is 25° C.) at the time of the application. Thereby the viscosity of the phosphor coating liquid is reduced, facilitating the movements of the first phosphor particles 61. In this case, the amounts of the movements of the first phosphor particles 61 are increased. Thus, the amounts of the movements of the first phosphor particles 61 toward the temporary support side are adjusted by controlling the temperature of the phosphor coating liquid at the time of the application.

Figure 12:
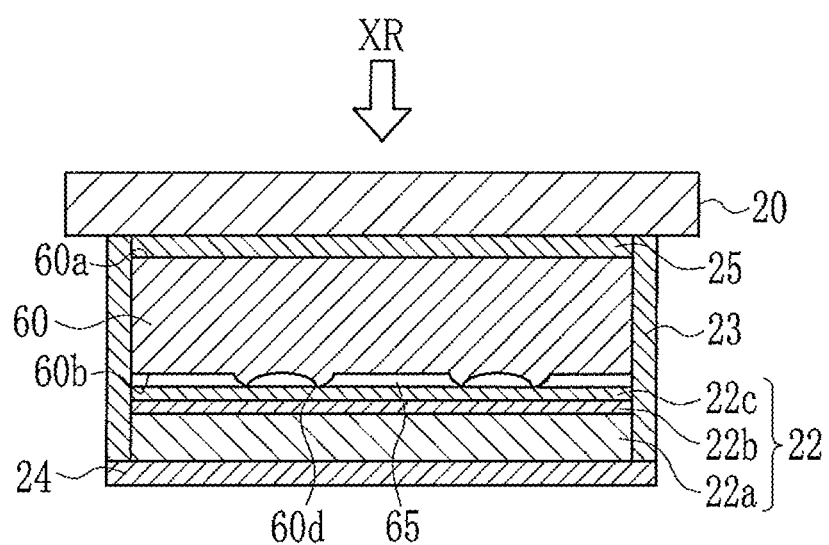
FIG. 12 is a vertical cross-sectional view of a radiation image detection device according to the second embodiment.

As shown in FIG. 12, a surface 60a, which has been on the temporary support side, of the wavelength converting layer 60 thus formed is bonded to the solid state detector 20 through the bonding agent layer 25. A surface 60b, which has been opposite to the temporary support side, of the wavelength converting layer 60 is bonded to the light reflective layer 22c.

Figure 13:
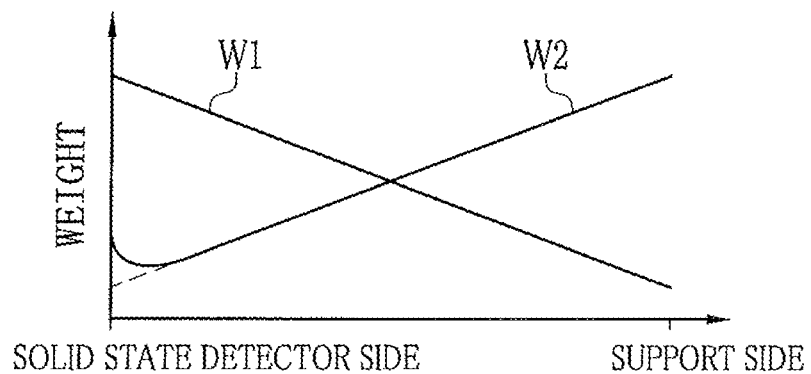
FIG. 13 is a graph illustrating a relationship between the space-filling ratio of the first and second phosphor particles and the weight ratio.
Figure 14:
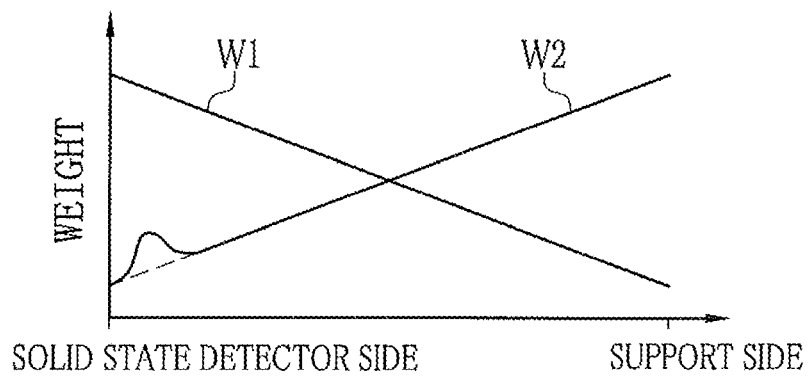
FIG. 14 is a graph illustrating a relationship between the space-filling ratio of the first and second phosphor particles and the weight ratio.

As shown in FIGS. 13 and 14, in regions close to the solid state detector 20 side on graphs, the weight W2 of the second phosphor particles 62 may not increase monotonously from the solid state detector 20 side toward the support 22 side, depending on the weight ratio WR. This is caused by the first phosphor particles 61 which block or prevent the second phosphor particles 62 from lifting in a direction toward the coated surface during drying of the phosphor coating liquid. On the contrary, the second phosphor particles 62 hardly block the first phosphor particles 61 because the first phosphor particles 61 are greater than the second phosphor particles 62 in diameter. Hence the weight W1 of the first phosphor particles 61 monotonously decreases from the solid state detector 20 side toward the support 22 side. FIG. 13 illustrates that the weight W2 is increased monotonously after it is reduced from the solid state detector 20 side toward the support 22 side. FIG. 14 illustrates that the weight W2 is increased monotonously after it is increased and reduced from the solid state detector 20 side toward the support 22 side.

Figure 15A:
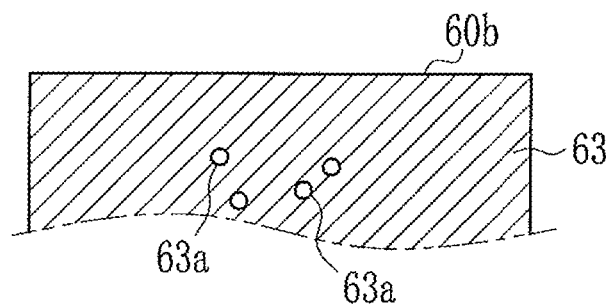
FIGS. 15A-15D illustrate a cause of a blister.
Figure 15B:
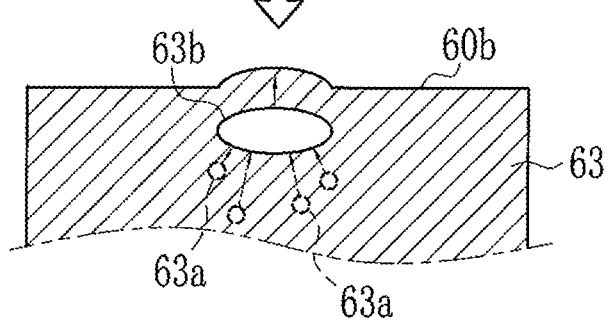
Figure 15C:
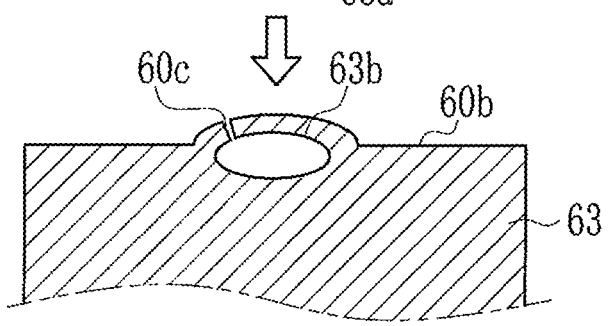
Figure 15D:
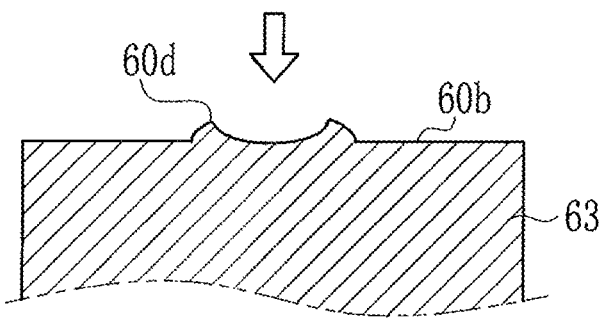

In this embodiment, when the phosphor coating liquid is applied to the temporary support and dried, a swelling or "blister" may occur on a coated surface (the surface 60b of the wavelength converting layer 60). During the drying of the phosphor coating liquid, the drying advances from the surface 60b side (the coated surface side). As shown in FIG. 15A, the blister is caused by residual solvents 63a, being residual volatile solvents not volatilized, in the binder 63 which is formed by drying the phosphor coating liquid. As shown in FIG. 15B, the residual solvents 63a clump together (flocculate) to form an aggregate 63b as the phosphor coating liquid is dried. The aggregate 63b pushes up the surface 60b as it moves upward to come out of the binder 63 and thus the blister is formed. As shown in FIG. 15C, a crack 60c appears between the aggregate 63b and the surface 60b as the blister further swells. The solvent volatilized from the aggregate 63b is released through the crack 60c. As a result, as shown in FIG. 15D, a caldera or crater-like protrusion 60d is formed due to the blister.

The diameter of the caldera-like protrusion 60d is in the order of several millimeters to 1 cm. An amount or height of the protrusion 60d protruded from the surface 60b is in the order of 100 to 200 μm. The thickness of the wavelength converting layer 60 is in the order of 300 μm.

The blister tends to occur as the average particle diameter D1 of the first phosphor particles 61 in the proximity of the surface 60b increases because the first phosphor particles 61 with the large particle diameters prevent the volatile solvents from moving up toward the surface 60b side during the drying. In this embodiment, however, drying time of the phosphor coating liquid is extended and thereby a large amount of the binder 63 is moved to the coated surface side (the surface 60b side) of the phosphor coating liquid. Hence, the amount of the first phosphor particles 61 is small on the surface 60b side. As a result, the occurrence of the blister is reduced. As shown in FIG. 12, the protrusion 60d due to the blister causes an air layer 65 between the surface 60b of the wavelength converting layer 60 and the light reflective layer 22c. The air layer 65 increases reflectivity of light between the wavelength converting layer 60 and the light reflective layer 22c and contributes to high sensitivity because a refractive index of the air layer 65 is lower than that of the wavelength converting layer 60.

In this embodiment, the protrusion 60d on the surface 60b is advantageous to the sensitivity properties. For this reason, the use of the first phosphor particles 61 with the large average particle diameter D1 is allowed. For example, as shown in FIG. 10, the first phosphor particles 61 with the average particle diameter D1 of 10 μm, which allow the space-filling ratio SFR of 75% at the maximum, are used and thereby the sensitivity is further improved.

A blister does not occur on the other surface 60a of the wavelength converting layer 60. Hence, the bonding agent layer 25 has high adhesion. The air layer hardly occurs between the surface 60a and the bonding agent layer 25. As a result, reflection or scattering of light hardly occurs. This is also advantageous in achieving high sensitivity and high sharpness.

In this embodiment, the radiation XR is incident on the surface 60a of the wavelength converting layer 60. A main light emission region in the wavelength converting layer 60 is on the surface 60a side. Hence, the "blister" does not affect the light emission. This is advantageous in achieving high sharpness.

Figure 16:
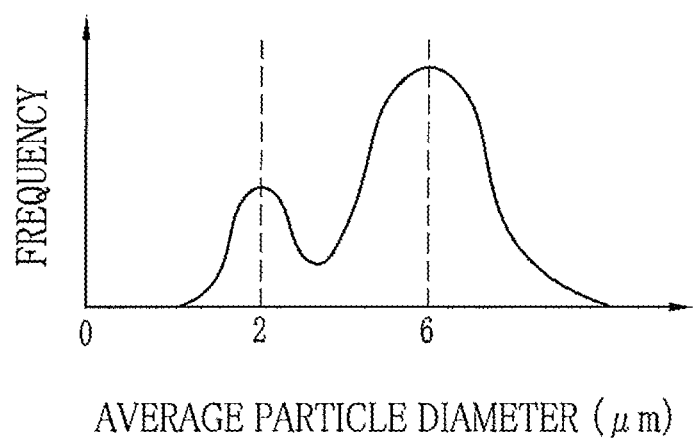
FIG. 16 is a graph illustrating an example of frequency distribution of the average particle diameters in the wavelength converting layer according to the second embodiment.

Whether the wavelength converting layer is a two-particle type, in which two types of phosphor particles different in diameter or size are dispersed, is detected using the above-described Fisher Sub-Sieve Sizer method. In the case where the wavelength converting layer is the two-particle type and a difference between the average particle diameters of the two types of the phosphor particles is large (D1=6 μm, D2=2 μm, for example), two peaks appear evidently in frequency distribution of the average particle diameters as shown in FIG. 16.

Third Embodiment

In the second embodiment, the two types of phosphor particles which differ in size are dispersed in the binder and thereby the wavelength converting layer is formed. Instead, three types of phosphor particles which differ in size may be dispersed in a binder to form a wavelength converting layer. In this case, small phosphor particles enter the spaces between other phosphor particles and become embedded in the spaces. Hence, the space-filling ratio of the phosphor particles is further improved, resulting in further improvement of the image quality.

Figure 17:
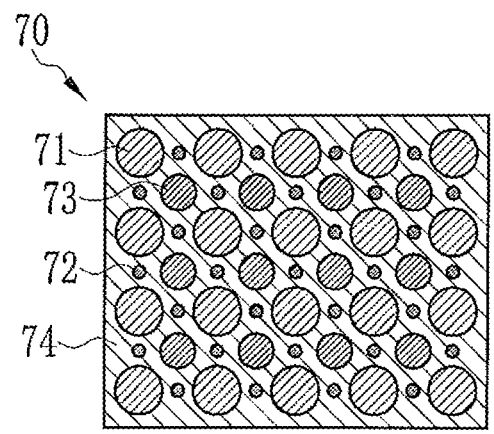
FIG. 17 is a lateral cross-sectional view cutting a wavelength converting layer of a third embodiment in a direction orthogonal to the radiation.

In a third embodiment, a wavelength converting layer 70 shown in FIG. 17 is used. The wavelength converting layer 70 is a dispersion of first phosphor particles 71, second phosphor particles 72, and third phosphor particles 73, which differ in size, in a binder 74. The average particle diameter of the first phosphor particles 71 is preferably greater than or equal to 9 μm and less than or equal to 12 μm, and more preferably in the order of 10 μm. The average particle diameter of the second phosphor particles 72 is preferably greater than or equal to 1 μm and less than 5 μm, and more preferably in the order of 2 μm. The average particle diameter of the third phosphor particles 73 is greater than or equal to 5 μm and less than 9 μm, and preferably in the order of 6 μm.

The first phosphor particles 71, the second phosphor particles 72, and the third phosphor particles 73 may be formed of the same material, or materials different from each other. A weight ratio among the first phosphor particles 71, the second phosphor particles 72, and the third phosphor particles 73 is preferably approximately 5:2:3. The space-filling ratio of the first to third phosphor particles 71-73 in the wavelength converting layer 70 is preferably greater than or equal to 68%.

Figure 18:
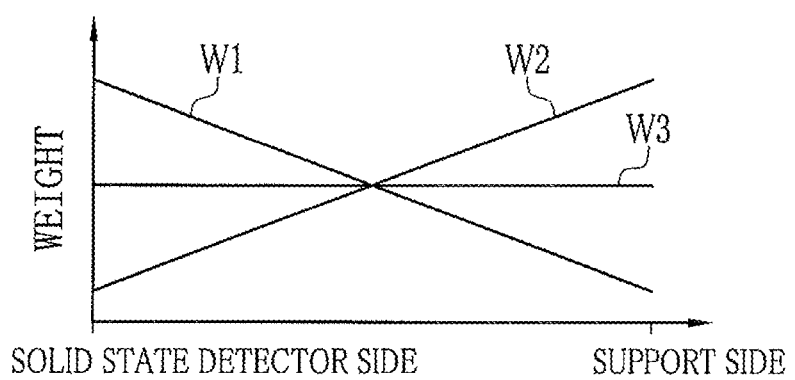
FIG. 18 is a graph illustrating changes in weight of first to third phosphor particles in the thickness direction of the wavelength converting layer.

In FIG. 18, the weight W1 of the first phosphor particles 71 per unit thickness of the wavelength converting layer 70 gradually decreases from the solid state detector 20 side toward the support 22 side. On the contrary, the weight W2 of the second phosphor particles 72 per unit thickness of the wavelength converting layer 70 gradually increases from the solid state detector 20 side toward the support 22 side. The weight W3 of the third phosphor particles 73 per unit thickness of the wavelength converting layer 70 hardly changes in the thickness direction.

As described above, on the solid state detector 20 side, the first phosphor particles 71 have the highest space-filling ratio, followed by the third phosphor particles 73 and the second phosphor particles 72, in descending order. On the support 22 side, the second phosphor particles 72 have the highest space-filling ratio, followed by the third phosphor particles 73 and the first phosphor particles 71, in descending order. The first phosphor particles 71 with the large average particle diameter are mainly present on the solid state detector 20 side. The second phosphor particles 72 with the small average particle diameter are mainly present on the support 22 side. Thereby an image with high sensitivity and high sharpness is produced. A relationship between the weight W2 of the second phosphor particles 72 and the weight W3 of the third phosphor particles 73 on the solid state detector 20 side may be reversed, depending on the average particle diameters of the first to third phosphor particles 71 to 73. In this embodiment, in a region close to the solid state detector 20 side on the graph, the weight W2 of the second phosphor particles 72 may not increase monotonously from the solid state detector 20 side to the support 22 side.

In order to produce the wavelength converting layer 70, a phosphor coating liquid in which the first phosphor particles 71, the second phosphor particles 72, and the third phosphor particles 73 are dispersed in a solution of the binder 74 is applied to the temporary support and dried, in a manner similar to the second embodiment. A surface, of the wavelength converting layer 70 thus produced, on the temporary support side is bonded to the solid state detector 20. Components other than the above in this embodiment are the same as those in the second embodiment.

As described above, in this embodiment, the blister may appear on the coated surface while the phosphor coating liquid is dried. In this embodiment, however, the occurrence of the blister is reduced because the amount of the first phosphor particles 71 with the large average particle diameter is small on the coated surface side of the phosphor coating liquid. For this reason, it is feasible to use the first phosphor particles 71 with large average particle diameter of 10 μm. Other effects of this embodiment are the same as those of the second embodiment.

The wavelength converting layer may be formed by dispersing four or more types of phosphor particles which differ in average particle diameter in a binder.

Other Embodiments

In the above embodiments, the phosphor coating liquid is applied to the temporary support and the phosphor particles with the large average particle diameter move or sink under their own weight to the temporary support side. Thereby the weight (space-filling ratio) on the temporary support side is increased. Instead, a surface active agent may be deposited on the surface of the phosphor particle. The phosphor particles may be moved or lifted to the opposite side of the temporary support due to the buoyant force caused by the surface active agent. In the case where the surface active agent is deposited on the phosphor particles with different sizes and then the phosphor particles are dispersed in the binder, the buoyant force increases with the size of the average particle diameter. This facilitates the movements of the phosphor particles toward the opposite side of the temporary support. In this case, the surface, of the wavelength converting layer, opposite to the temporary support is bonded to the solid state detector 20.

In the above embodiments, the wavelength converting layer is bonded to the solid state detector through the bonding agent layer. Instead, the wavelength converting layer may be in direct contact with and abut against the solid state detector.

Various changes and modifications are possible in the present invention and may be understood to be within the present invention.

What is claimed is:

1. A radiation image detection device comprising:
   a wavelength converting layer for converting radiation into light, the wavelength converting layer being a single phosphor layer in which at least first phosphor particles and second phosphor particles are dispersed in a binder, the first phosphor particles having a first average particle diameter, the second phosphor particles having a second average particle diameter smaller than the first average particle diameter; and
   a solid state detector for detecting the light and thereby generating image data, the solid state detector and the wavelength converting layer being disposed in this order from a radiation-incident side on which the radiation from a radiation source is incident at the time of imaging;
   wherein, a weight of the first phosphor particles per unit thickness of the wavelength converting layer decreases with increasing distance from the solid state detector.

2. The radiation image detection device according to claim 1, wherein a weight of the second phosphor particles per unit thickness of the wavelength converting layer is smaller on a solid state detector side than on an opposite side of the solid state detector.

3. The radiation image detection device according to claim 2, wherein the weight of the second phosphor particles per unit thickness of the wavelength converting layer increases with increasing distance from the solid state detector.

4. The radiation image detection device according to claim 3, wherein a phosphor coating liquid, in which the first and second phosphor particles are dispersed in a solution of the binder, is applied to a temporary support and dried and then peeled off from the temporary support and thereby the wavelength converting layer is formed, and a surface of the wavelength converting layer on a temporary support side is placed on the solid state detector side.

5. The radiation image detection device according to claim 4, wherein a light reflective layer is provided over the wavelength converting layer and opposite the solid state detector.

6. The radiation image detection device according to claim 5, wherein the wavelength converting layer has a protrusion on a surface on a light reflective layer side.

7. The radiation image detection device according to claim 6, wherein the solid state detector is bonded to the wavelength converting layer through a bonding agent layer or the solid state detector is directly in contact with and abut against the wavelength converting layer.

8. The radiation image detection device according to claim 7, wherein a support is provided over the light reflective layer and opposite the wavelength converting layer, and the wavelength converting layer and the support are bonded through the light reflective layer by heating and compression.

9. The radiation image detection device according to claim 7, wherein a weight ratio of the first phosphor particles to the second phosphor particles is 20% to 40%.

10. The radiation image detection device according to claim 9, wherein the first average particle diameter is greater than or equal to 5 μm and less than or equal to 12 μm and the second average particle diameter is greater than or equal to 1 μm and less than 5 μm.

11. The radiation image detection device according to claim 10, wherein a space-filling ratio of the first and second phosphor particles in the wavelength converting layer is greater than or equal to 68%.

12. The radiation image detection device according to claim 7, wherein the phosphor particles are formed of $A_2O_2S$: X, where A is one of Y, La, Gd, and Lu, and X is one of Eu, Tb, and Pr.

13. The radiation image detection device according to claim 7, further comprising a side covering member for covering outer edges of the wavelength converting layer.

14. A radiation imaging system comprising:
(A) a radiation source for applying radiation to a subject; and
(B) a radiation image detection device for detecting a radiation image based on the radiation passed through the subject, the radiation image detection device comprising:
a wavelength converting layer for converting the radiation into light, the wavelength converting layer being a single phosphor layer in which at least first phosphor particles and second phosphor particles are dispersed in a binder, the first phosphor particles having a first average particle diameter, the second phosphor particles having a second average particle diameter smaller than the first average particle diameter; and
a solid state detector for detecting the light and thereby generating image data of the radiation image, the solid state detector and the wavelength converting layer being disposed such that the radiation passed through the solid state detector is incident on the wavelength converting layer;
wherein a weight of the first phosphor particles per unit thickness of the wavelength converting layer decreases with increasing distance from the solid state detector.

* * * * *